US007169151B1

(12) United States Patent
Lytinas

(10) Patent No.: US 7,169,151 B1
(45) **Date of Patent: *Jan. 30, 2007**

(54) BONE REGENERATION DEVICE FOR LONG BONES, AND METHOD OF USE

(75) Inventor: Michael Lytinas, Boston, MA (US)

(73) Assignee: KCI Licensing, Inc., San Antonio, TX (US)

( * ) Notice: Subject to any disclaimer, the term of this patent is extended or adjusted under 35 U.S.C. 154(b) by 592 days.

This patent is subject to a terminal disclaimer.

(21) Appl. No.: 10/410,610

(22) Filed: Apr. 10, 2003

(51) Int. Cl.
*A61F 5/00* (2006.01)

(52) U.S. Cl. .......................................................... 606/86

(58) Field of Classification Search .................. 606/86, 606/53, 60

See application file for complete search history.

(56) References Cited

U.S. PATENT DOCUMENTS

| | | | |
|---|---|---|---|
| 4,822,278 A | 4/1989 | Oliva et al. | |
| 5,019,086 A | 5/1991 | Neward | |
| 5,224,947 A | 7/1993 | Cooper et al. | |
| 5,636,643 A | 6/1997 | Argenta et al. | |
| 5,645,081 A | 7/1997 | Argenta et al. | |
| 5,807,230 A | 9/1998 | Argenta et al. | |
| 5,810,840 A | 9/1998 | Lindsay | |
| 5,935,136 A | 8/1999 | Hulse et al. | |
| 5,964,733 A | 10/1999 | Laabs et al. | |
| 6,086,587 A | 7/2000 | Hawk | |
| 6,345,623 B1 | 2/2002 | Heaton et al. | |
| 6,359,189 B1 | 3/2002 | Fleischmann | |
| 6,398,767 B1 | 6/2002 | Fleischmann | |
| 6,491,693 B1 | 12/2002 | Lytinas | |
| 6,553,998 B2 | 4/2003 | Heaton et al. | |
| 6,555,729 B1 | 4/2003 | Fleischmann | |
| 6,557,487 B1 | 5/2003 | Fleischmann | |
| 6,673,028 B1 | 1/2004 | Argenta et al. | |
| 6,712,851 B1 * | 3/2004 | Lemperle et al. | 623/16.11 |
| 6,770,794 B2 | 8/2004 | Fleischmann | |
| 6,814,079 B2 | 11/2004 | Heaton et al. | |
| 6,863,022 B2 | 3/2005 | Fleischmann | |
| 2001/0029956 A1 | 10/2001 | Argenta et al. | |
| 2002/0115952 A1 * | 8/2002 | Johnson et al. | 602/41 |
| 2003/0225347 A1 | 12/2003 | Argenta et al. | |
| 2004/0039391 A1 | 2/2004 | Argenta et al. | |
| 2004/0122434 A1 | 6/2004 | Argenta et al. | |
| 2005/0028828 A1 | 2/2005 | Heaton et al. | |
| 2005/0043659 A1 * | 2/2005 | Challis et al. | 602/5 |
| 2005/0283105 A1 | 12/2005 | Heaton et al. | |

OTHER PUBLICATIONS

Fleischmann, Wilhelm; "Vakuumversiegelug zur Behandlung von Problemwunden"; [Vacuum Sealing for the Treatment of Problematic Wounds]; Hartmann WundForum ; Mar. 1994; pp. 3-9.

(Continued)

*Primary Examiner*—Eduardo C. Robert
*Assistant Examiner*—Michael J. Araj

(57) ABSTRACT

A method of stimulating bone regeneration in a discontinuous section of a long bone in a subject requiring same, comprising the step of applying to said discontinuous section of the bone an effective vacuum for an effective length of time. A device for carrying out the method consisting of a sealable tubular-shaped sleeve or cuff that fits snugly and sealably around the bone section to be treated and that can be evacuated via a port that is integral to the sleeve or port.

20 Claims, 1 Drawing Sheet

1
2
3
4
5
6
7

OTHER PUBLICATIONS

Fleischmann, Wilhelm; et al; "Vakuumversiegelung zur Behandlung des Weichteilschadens bei offenen Frakturen"; [Vacuum Sealing for the Treatment of Soft Tissue Injury in Open Fractures]; Unfallchirug; 1993, vol. 96, pp. 488-492.

Fleischmann, Wilhelm, et al;"Verletzungen der Wirbelsaule, Gefahren und Komplikationen der Therapie"; [The Thoratic Spine, Risks and Complications of the Therapy]; OP Journal; 1990; pp. 31-44.

Fleischmann; Wilhelm, et al; "Treatment of Bone and Soft Tissue Defects in Infected Nonunion"; *Acta Orthopaedica Belgica* vol. 58, Suppl. 1—1992; pp. 227-233.

Fleischmann, Wilhelm, et al; "Vacuum sealing: indication, technique, and results; European Journal of Orthopaedic Surgery & Traumatology"; Springer-Verlag; 1995; pp. 37-40.

Argenta, Louis C., et al; "Vacuum-Assisted Closure: A New Method for Wound Control and Treatment: Clinical Experience"; Annals of Plastic Surgery; vol. 38, No. 6, Jun. 1997; pp. 563-576.

* cited by examiner

BONE REGENERATION DEVICE FOR LONG BONES, AND METHOD OF USE

FIELD OF THE INVENTION

The invention is concerned with local bone regeneration for long bones. More specifically, the invention relates to the use of locally-applied vacuum to stimulate osteoblastic activity in long bones with discontinuity defects.

BACKGROUND OF THE INVENTION

Osteogenesis, the growth of new bone, is a part of the normal healing process, and involves recruiting and activating osteoblast cells in bone. This can be a slow process, particularly in the elderly and after severe trauma to the bone and after disease. The ability to accelerate osteogenesis would speed the healing process after trauma and after orthopedic and dental procedures. Methods to accelerate the process, particularly in local areas of bone, have been a holy grail for scientists for many years.

Current techniques of bone regeneration include: traditional methods such as distraction osteogenesis in which bone is pulled in an appropriate direction to stimulate growth, and bone grafting; and, experimental techniques that include use of drugs such as OP-1 that stimulate osteoblasts, implanting biomaterials laced with molecular signals designed to trigger the body's own repair mechanism, injecting bone marrow stem cells into the affected areas, and, transfusing cells that carry genes that code for bone-repair proteins. None of these methods are yet totally satisfactory, for a host of reasons. For a review of this subject see: Service, *Science,* 289:1498 (2000)

Distraction osteogenesis requires a bulky device and requires a very long period before positive results are seen. Bone grafting is limited by the quantity and quality of the patient's bone available for grafting. Biocompatible polymeric matrices without or with natural or recombinant bone morphogenic proteins suffer from a need for very large and very expensive quantities of these signal proteins. The gene therapy procedure suffers from the general problems of gene therapy in general. The use of the stem cell approach is greatly limited by the scarcity and expense of such cells; for example, in 50-year olds, there is only one stem cell in 400,000 bone marrow cells (see Service, 2000, above.

Applicant has previously described a device that applies subatmospheric pressures to a fractured or lesioned area of a flat bone (e.g., scapula), and thereby promotes osteogenesis and consequent bone healing in such areas (Lytinas, U.S. Pat. No. 6,491,683, which is incorporated herein by reference). However, for anatomical reasons such a device is not suitable for non-flat long bones of the upper and lower extremities, particulary where blunt trauma from accidents and/or projectiles produces in the long bone discontinuous defects leaving gaps of 2.5 cm and more. In the past such discontinuous defects have been treated orthopedically by grafting into the discontinuity pieces of bone taken from elsewhere in the body. More often than not, such grafting does not completely fill the discontinuity, thereby leading to poor healing (fibrous displacement) and shortened extremities.

Clearly, there is an acute need for a safe, simple, rapid, inexpensive and efficient device and method for producing osteogenesis in discontinuous regions of long bones. Such a device and method, based in principle on the vacuum technique discovered by the applicant (U.S. Pat. No. 6,491,693) has now been discovered, and is described below.

SUMMARY OF THE INVENTION

A device and method for producing bone regeneration (osteogenesis) in a discontinuous local section of a long bone in a subject requiring same, comprising the step of applying to the local section of the bone a vacuum (subatmospheric pressure) for an effective period of time.

In one embodiment, the discontinuous section of the long bone is sealed from the atmosphere with a flexible, sterilizable sleeve or cuff device of a dimension and curvature suitable to enclose and fit sealably tightly over the discontinuous or fractured section of the long bone, the device being connected through a sealable exit port to a source of vacuum, such that the discontinuous section of the long bone can be evacuated for an appropriate length of time.

DETAILED DESCRIPTION OF THE INVENTION

Figure 1:
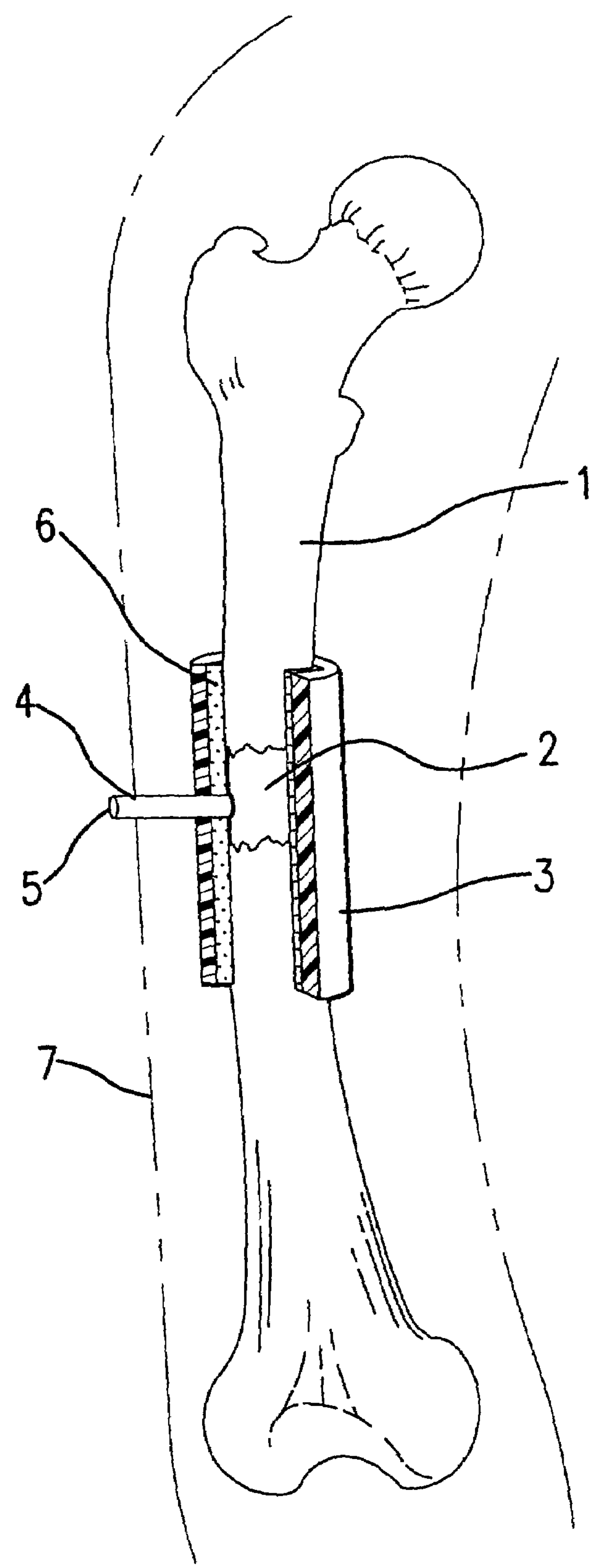
FIG. 1 is a sketch of the sleeve/cuff device of the invention.

The essence of the invention is the production of bone regeneration (osteoblastic cell-induced osteogenesis) in a desired section of a long bone by the application to this section a vacuum (within the context of this specification the term vacuum is to be considered synonymous with subatmospheric pressure) for an effective length of time.

The method can be applied to any long bone in humans or animals. It can be applied to a wide variety of medical conditions, e.g., a bone that has been shattered by such trauma that produces a discontinuous section that requires osteogenesis; a bone that requires lengthening; a bone that needs reshaping, as after an accident; a bone after surgical removal of a cancerous or cystic section of the bone; and, in bone resorption areas (alveolar region).

The device of the invention is suitable for a variety of long bones, including a femur, a clavicle, ribs, humerus, ulna and radius, carpal and metacarpal bones and their phalanges, tibia, fibula, and, tarsal and metatarsal bones and their phalanges, among others.

At the heart of the invention is a device that produces the vacuum on the discontinuous or fractured section of the long bone. A highly preferred device is an evacuatable sleeve or cuff (the two terms are used interchangeably) that can be fitted around the discontinuous section or fracture of the bone and that can be maintained under vacuum through a port. The evacuation port is continuous with both the interior of the sleeve or cuff and the skin surrounding the bone being treated so that repeated re-evacuations may be easily applied by medical personnel.

In FIG. 1, 1 is a representative example of a long bone being treated; 2 is a representative discontinuity defect; 3 is the sleeve or cuff that encloses the bone both above and below the discontinuity; 4 is the vacuum port that extends from the interior of the sleeve or cuff to outside the skin; 5 is the sealable port orifice that is connected to a vacuum pump or the like; 6 depicts sealant that is placed between the sleeve or cuff and the bone, above and below the discontinuity; and, 7 is the skin.

The sleeve or cuff should be composed of a flexible, sterilizable (e.g., autoclavable) material. It may be made of a light biocompatible metal or plastic, and its walls should be sufficiently thick so as not to collapse under vacuum. Snugness of the sleeve or cuff device is accomplished, in part, by fabricating the device so that the curvature of the portion resting against the bone is designed to fit the particular bone being treated, and, in part, by the flexibility of the sleeve or cuff. Sleeves or cuffs with a wide variety of sizes and shapes may be fabricated by well-known methods and kept on hand under sterile conditions.

The sleeve or cuff of the inventive device is hermetically glued to the bone above and below the discontinuity section with any appropriate surgical glue, e.g., an elastic silicone Nexaband Liquid, VPL, Inc. without or with glues of the type of KRAZY GLUE. It is important that the glue have elastic properties so that the vacuum seal will not be broken if the bone moves in place.

The sleeve or cuff, once attached to the bone, is evacuated by a vacuum pump (e.g., Nalgene vacuum pump, although any other vacuum pump is suitable) by means of the port (4 and 5 in FIG. 1). Following attainment of the desired degree of vacuum, the connection between the device and the pump is sealed. As the port extends through the skin, it is readily accessible for repeated evacuations of the system. The degree of vacuum is determined by the extent of the discontinuityl. For example, as little as 30 in. Hg is sufficient to induce bone regeneration in a skeletal bone. The vacuum port may also be fitted with an attached vacuum measuring gauge.

The device is maintained in place for an appropriate length of time before being removed. Determination of this appropriate length of time is based on the clinical condition being treated and the degree of regeneration required. This determination does not require undue experimentation by the medical or dental surgeon applying the technique.

The progress of bone regeneration may be followed radiographically, as a plastic version of the inventive device is radiolucent and new bone is not. The osteoid precursor stage of bone regeneration may not, however, always be visible by X-ray. At an appropriate time, the inventive device may be removed surgically, preferably by cutting it away from the bone by, for example, a dental burr.

The following example merely provides an embodiment of the inventive method, and should not be construed as limiting the claims in any way.

EXAMPLE 1

The Surgical Protocol

Under sterile conditions, the bone to be treated is reached surgically. Skin, fat, muscles, etc. are blunt-resected from the bone.

The autoclaved sleeve or cuff device is slipped around the desired discontinuity section of the bone, and sealed to the bone with surgical glue (e.g., Nexaband liquid, Veterinary Products Laboratories, Inc.).

The vacuum port of the device is attached to a vacuum pump, and the device evacuated to the desired pressure, e.g., about 30 in. Hg. At this point the vacuum port is sealed so as to maintain the vacuum. The subcutaneous tissues are closed with sutures, e.g., a 4-0 Dexonsuture, and the skin sutured closed.

The degree of vacuum can be monitored by a vacuum gauge attached to the vacuum port.

At an appropriate length of time, e.g., about four weeks, the device (still well-sealed) is removed from the long bone. An osseoid thickening of the bone at the site of the treatment will be noted.

I claim:

1. A device for stimulating new bone formation in a discontinuous defective section of a long bone, comprising a sleeve or cuff of a dimension and curvature fabricated to fit snugly around said section of bone, wherein said device is composed of an evacuatable, sterilizable, flexible, sealable material capable of being elastically sealed to said long bone, and wherein said vacuum is imposed within said sleeve or cuff through a sealable port that extends from the interior or said sleeve or cuff through the skin to the exterior of the body.

2. The device according to claim 1, wherein said long bones are selected from a group consisting of a femur, a clavicle, ribs, humerus, ulna, and radius, carpal and metacarpal bones and their phalanges, tibia, fibula, and, tarsal and metatarsal bones and their phalanges.

3. The device according to claim 1, wherein said vacuum is monitored by a pressure gauge attached to said port.

4. The device according to claim 1, further comprising a vacuum pump connected to the sealable port to apply the vacuum.

5. The device according to claim 1, further comprising a sealant applied between the sleeve or cuff and the bone above and below the discontinuous defective section.

6. The device according to claim 1, wherein the discontinuous defective section of the long bone is a bone fracture.

7. A method of stimulating new bone formation in a long bone with discontinuity defects in a subject with a medical condition requiring same, comprising the step of applying to said discontinuous section of said bone an effective amount of vacuum for an effective period of time.

8. The method according to claim 7, wherein said medical condition is selected from the group consisting of a bone that has been shattered by such trauma that produces a discontinuous section that requires osteogenesis; a bone that requires lengthening; a bone that needs reshaping; a bone after surgical removal of a cancerous or cystic section of the bone; and in bone resorption areas (alveolar region).

9. The method according to claim 7, wherein said long bones are selected from a group consisting of a femur, a clavicle, ribs, humerus, ulna and radius, carpal and metacarpal bones and their phalanges, tibia, fibula, and, tarsal and metatarsal bones and their phalanges.

10. The method according to claim 7, wherein the effective amount of vacuum is greater than or equal to about 30 in Hg.

11. The method according to claim 7, wherein the effective amount of vacuum is subatmospheric.

12. The method according to claim 7, wherein the effective period of time is about four weeks.

13. The method according to claim 7 further comprising:
determining the effective period of time based on the medical condition being treated and the degree of bone regeneration required.

14. The method according to claim 7 further comprising:
determining the effective period of time by radiographically viewing bone regeneration in the long bone.

15. The method according to claim 7 further comprising:
positioning a sleeve or cuff around the discontinuity defects in the long bone; and
wherein applying an effective vacuum further comprises applying the vacuum to the long bone through the sleeve or cuff.

16. The method according to claim 15 further comprising:
surgically exposing the long bone prior to positioning the sleeve or cuff, thereby creating a surgical wound; and
closing the surgical wound after positioning the sleeve or cuff.

17. The method according to claim 15 further comprising:

measuring the vacuum applied to the long bone;

reapplying vacuum as necessary during the effective period of time to maintain the effective amount of vacuum;

determining the effective period of time by radiographically viewing bone regeneration in the long bone;

ceasing the application of vacuum following bone regeneration; and removing the sleeve or cuff following the effective period of time.

18. The method according to claim 17, wherein the effective amount of vacuum is subatmospheric.

19. The method according to claim 17 further comprising:

surgically exposing the long bone prior to positioning the sleeve or cuff, thereby creating a surgical wound; and closing the surgical wound after positioning the sleeve or cuff.

20. The method according to claim 7, wherein the discontinuous section of the long bone is a bone fracture.

* * * * *

UNITED STATES PATENT AND TRADEMARK OFFICE

CERTIFICATE OF CORRECTION

PATENT NO. : 7,169,151 B1

APPLICATION NO. : 10/410610

DATED : January 30, 2007

INVENTOR(S) : Michael Lytinas

It is certified that error appears in the above-identified patent and that said Letters Patent is hereby corrected as shown below:

Column 1, line 50, replace “6,491,683” with --6,491,693--

Signed and Sealed this

First Day of May, 2007

JON W. DUDAS

*Director of the United States Patent and Trademark Office*